United States Patent [19]
Anderson

[11] Patent Number: 6,050,551
[45] Date of Patent: Apr. 18, 2000

[54] PORTABLE APPARATUS FOR DISTRIBUTING AND SELECTIVELY SEALING A VAPORIZED OR SMALL PARTICLE SUBSTANCE

[76] Inventor: Brent Gary Anderson, 4205 Greenfield La., Lake in the Hills, Ill. 60102

[21] Appl. No.: 09/004,363

[22] Filed: Jan. 8, 1998

[51] Int. Cl.$^7$ .................................................. B01D 47/00
[52] U.S. Cl. ................... 261/30; 261/104; 261/DIG. 17; 261/DIG. 65; 422/124; 239/56; 239/58
[58] Field of Search ............................ 261/104, DIG. 65, 261/DIG. 17, 30; 422/124; 239/53, 54, 55, 56, 57, 58, 59, 60

[56] References Cited

U.S. PATENT DOCUMENTS

| | | | |
|---|---|---|---|
| 2,988,283 | 6/1961 | Garfield | 239/57 |
| 3,527,405 | 9/1970 | Harding | 261/DIG. 65 |
| 3,694,545 | 9/1972 | Roth et al. . | |
| 3,923,934 | 12/1975 | Watkins | 261/DIG. 17 |
| 3,990,848 | 11/1976 | Corris . | |
| 4,059,422 | 11/1977 | Steiner | 261/DIG. 65 |
| 4,078,891 | 3/1978 | Madjar . | |
| 4,271,092 | 6/1981 | Sullivan et al. . | |
| 4,301,095 | 11/1981 | Mettler et al. . | |
| 4,374,571 | 2/1983 | Hirvela | 239/56 |
| 4,383,951 | 5/1983 | Palson . | |
| 4,432,938 | 2/1984 | Meetze, Jr. . | |
| 4,663,315 | 5/1987 | Hasegawa et al. . | |
| 4,666,638 | 5/1987 | Baker et al. . | |
| 4,840,770 | 6/1989 | Walz et al. . | |
| 5,047,234 | 9/1991 | Dickerson et al. . | |
| 5,050,798 | 9/1991 | Sullivan . | |
| 5,115,975 | 5/1992 | Shilling . | |
| 5,147,582 | 9/1992 | Holzner, Sr. et al. . | |
| 5,174,967 | 12/1992 | Fukuhara . | |
| 5,230,867 | 7/1993 | Kunze et al. . | |
| 5,234,162 | 8/1993 | Sullivan . | |
| 5,259,062 | 11/1993 | Pelonis . | |
| 5,324,490 | 6/1994 | Van Vlahakis et al. . | |
| 5,328,646 | 7/1994 | Bryson et al. . | |
| 5,342,584 | 8/1994 | Fritz et al. . | |
| 5,370,829 | 12/1994 | Kunze . | |
| 5,376,338 | 12/1994 | Zlotnik . | |
| 5,431,885 | 7/1995 | Zlotnik et al. . | |
| 5,498,397 | 3/1996 | Horng . | |
| 5,529,726 | 6/1996 | Glenn . | |
| 5,642,931 | 7/1997 | Gappelberg | 362/186 |

*Primary Examiner*—David A. Simmons
*Assistant Examiner*—Robert A. Hopkins
*Attorney, Agent, or Firm*—Niro, Scavone, Haller & Niro

[57] ABSTRACT

A portable apparatus for dispensing of vapor from a volatile insect repelling or animal attracting/repelling substance into the surrounding environment, which includes a body having an inlet and outlet means, a sealing means for selectively closing and opening the vent means, a substance containing means for containing the volatile, a motorized fan, and an electrical power source. The apparatus includes a sealing means to seal the volatile substance within the body of the apparatus when the device is not in use. An important feature is also the ability to transmit volatile insect repelling or animal attracting/repelling substance over a great area.

1 Claim, 4 Drawing Sheets

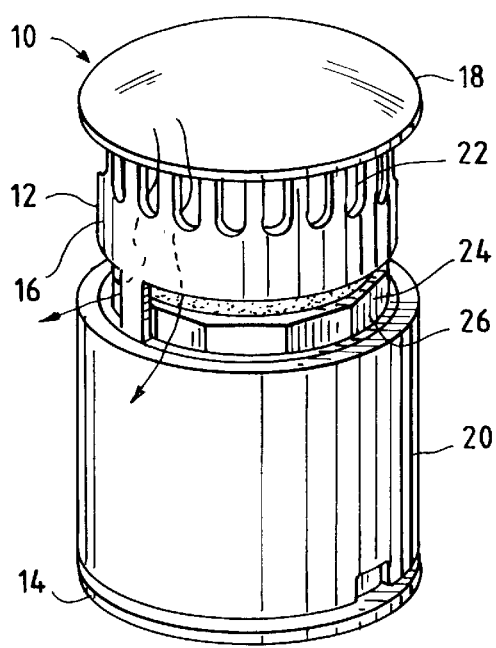
FIG. 1
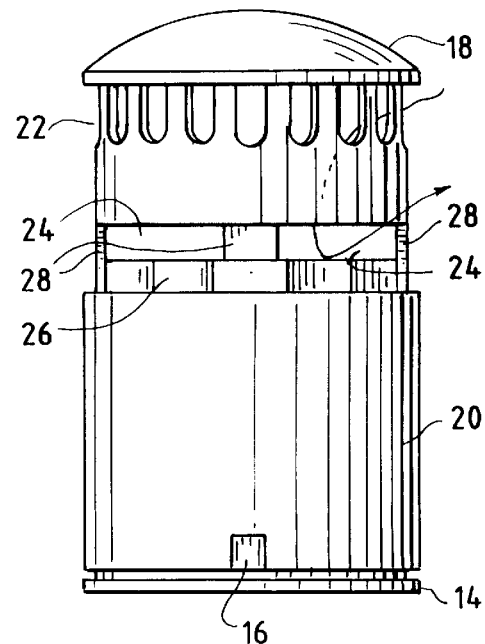
FIG. 2A
FIG. 2B
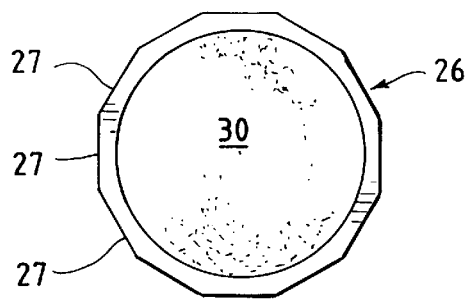
FIG. 2C
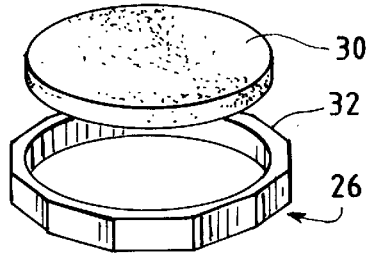
FIG. 2D
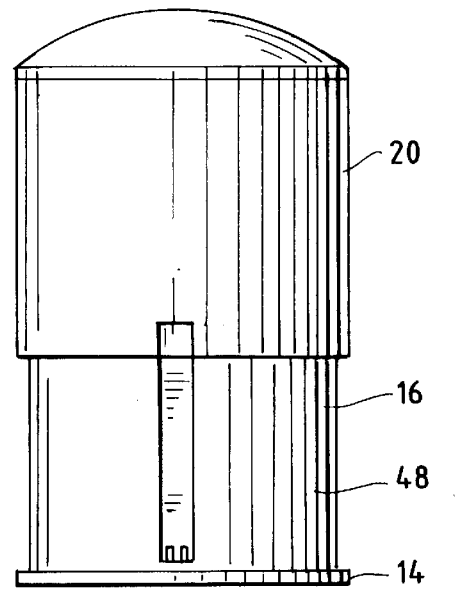

PORTABLE APPARATUS FOR DISTRIBUTING AND SELECTIVELY SEALING A VAPORIZED OR SMALL PARTICLE SUBSTANCE

BACKGROUND OF THE INVENTION

The present invention relates to devices for selectively distributing vaporized or small particle substances into the surrounding environment and, more particularly, to a portable, self-contained device for generating an air current for forcefully distributing vaporized or small particle substances into the surrounding environment.

Various devices exist for distributing vapors from volatile substances into the surrounding environment for such purposes as, for example, repelling or attracting insects or animals, or for adding a pleasant odor to the surrounding air. These devices include some type of container or medium for holding a gelled or solidified volatile substance, and vents for allowing vaporization of the substance. Typically, a medium such as a gel contains a very small percent of the active ingredient. Many of these devices are limited by the natural rate of vaporization of the substance and the natural surrounding air current for dispersion of the vapors. Some devices rely on a candle flame to cause volitilization, while others rely on an electric heat source or fan. Devices that utilize a candle flame emit undesirable by-products and may pose a fire or safety hazard. Existing devices using electric or other heat sources create a potential fire hazard. Some devices require an AC connection and are not portable. Most of these devices are limited to dispersing of vapors or particles in one general direction only. None of the known devices are portable, selectably sealed or opened, self-powered, omni-directional and wind or water resistant. A device having such characteristics is desirable for hunting, camping, yard use and other uses.

It is therefore an object of the invention to provide a portable, self-contained and self-powered, omni-directional, non-flame apparatus for dispersing vapors and small particle substances. It is a further object to make such a device durable, water and air tight, re-usable, versatile and practical. These and other objects and characteristics of the present invention will become apparent in the description and claims that follow.

SUMMARY OF THE INVENTION

The present invention is directed to, but not limited to, an apparatus comprising a housing system, a volatile or small particle substance-containing compartment, and inlet and outlet venting system, and an electric motor fan system. The housing system includes a body forming an outer housing adapted to rest on a generally horizontal surface or to be attached to an object or surface. A movable housing piece is provided that is adapted to selectively open and close the venting system and, optionally, to turn the fan system on and off. The substance-containing compartment comprises a chamber in the body that is designed to hold a substance or a medium that contains a substance, such as a saturated absorbent pad. The venting system comprises openings in the body that allow inward flow of air into the body upstream from the fan, and outward flow from the fan to the substance and, finally, out of the body. The electric motor and fan system comprise a conventional DC motor and any one of a variety of known fan blade designs. A self-contained power source, such as a battery compartment, powers the motor and fan.

BRIEF DESCRIPTION OF THE DRAWINGS

FIG. 1 is a perspective view of the substance dispersing apparatus of the present invention.

FIGS. 2A and 2B are front view of the apparatus of FIG. 1, shown in the "on" and "off" positions, respectively.

FIG. 2C is a top view of a component of the present invention.

FIG. 2D is an exploded, perspective view of the component of FIG. 2C.

DETAILED DESCRIPTION OF THE DRAWINGS

Figure 3A:
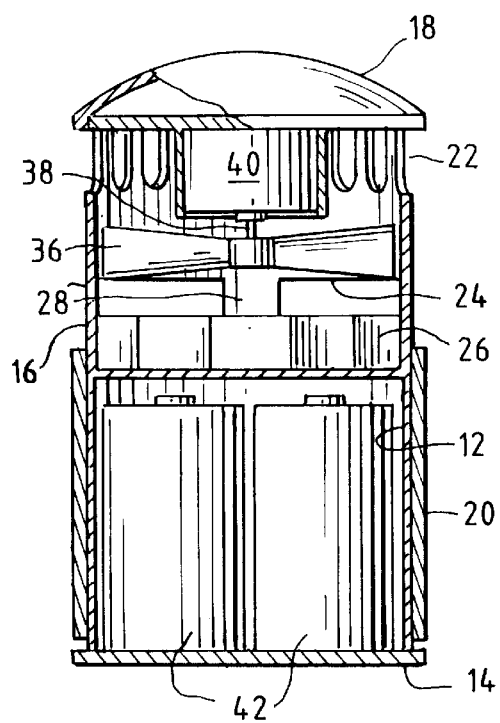
FIGS. 3A and 3B are front sectional view of the apparatus in FIGS. 2A and 2B, respectively.

As shown in FIG. 1, the apparatus (10) of the present invention comprises a body (12) having a generally flat base (14), a vertically extended wall section (16) and a top (18). The apparatus (10) also comprises a slideable wall section (20) adapted to fit around the walled section (16) and slide relative thereto. Inlet vents (22) and outlet vents (24) are provided. While the preferred embodiment shown in FIG. 1 utilizes a generally cylindrical-shaped structure formed by the base (14), walled seciton (16) and top (18), the present invention apparatus (10) is not limited to that particular shape. The present invention apparatus may also be in the shape of, for example, a cube or a prism or other desirable shape. A generally symmetrical shape is preferred to more easily produce even omni-directional dispersing of vapors or particles.

The slideable section (20) is adapted to translate vertically between an opened or "on" position as shown in FIG. 2A, and a closed or "off" position as shown in FIG. 2B. In the on position, the slideable section (20) is positioned down, adjacent to the base (14) do that the inlet and outlet vents (22, 24) are exposed to the environment. In the off position, the slideable section (20) is raised to a position adjacent to the top (18), covering and sealing the vents (22, 24). This prevents inadvertent release of the substance contained in the body (12) and the entry of moisture, dirt or other elements into the body (12). While the slideable section (20) is in the closed or off position, the lower portion of the walled section (16) serves as a solid outer wall.

As shown in FIG. 2A, the slideable section (20) is lowered to the on position to enable a substance or a substance-carrying article to be placed inside the body (12). In the preferred embodiment, the substance-carrying article is generally shaped like a disc (26) for convenient and secure fitting in the body (12). The disc (26) can be, more precisely, in the form of a polygon, as shown in FIGS. 2C and 2D, to provide flat surfaces (27) which facilitate press-fitting into the body (12). By constructing the disc (26) and the body (12) of a flexible plastic material, press-fitting is more readily achieved. As shown in the preferred embodiment, the body (12) forms three struts (28) at the outlet vent (24), whereby the struts (28) are adapted to receive straight sides of a polygon-shaped disc (26) for press fitting. In the preferred embodiment, the struts (28) are positioned around the circumference defined by the body (12) at 0 degrees, 90 degrees and 180 degrees to enable convenient insertion and removal of the disc (26). As shown in FIGS. 2C and 2D, an absorbent pad (30), such as a felt or sponge foam pad, is saturated with a volatile substance, such as citronella or game scent, and placed in or adhered to the disc (26). The disc (26) can be provided with vertical walls (32), as shown, to contain and support a pad (30) or other substance medium. The disc (26) and pad (30) can be made to be disposable or re-usable.

Figure 3B:
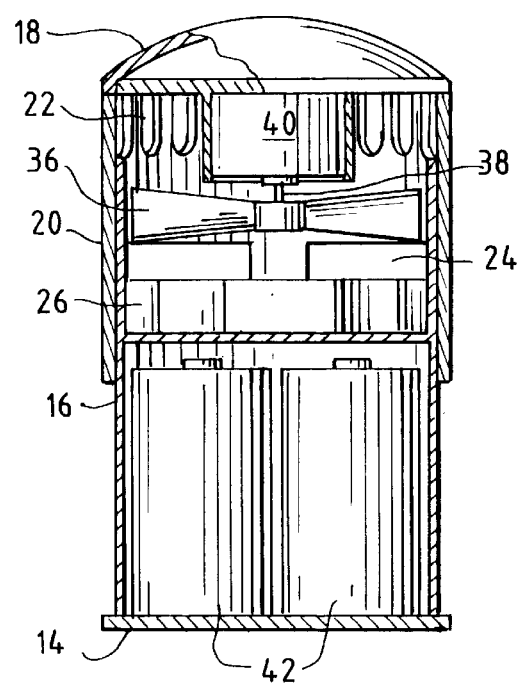

In FIGS. 3A–3B, there is shown a fan blade (36) fixed to a rotatable shaft (38) that is coupled to a DC motor (40) which is mounted to the top (18) inside the body (12). The DC motor (40) is in electrical communication with batteries (42) through conventional or known wiring arrangements (not shown). The batteries (42) are housed in a battery compartment, as shown, within the body (12). The fan blade (36) is configured to provide a downward air current drawing intake from the inlet vents (22) and being directed against the substance-carrying disc (26). The forced air, now containing vapor or solid particles, deflects back toward the fan (36) where additional forced air from the fan creates pressure inside the body (12) so that the vapor and particles are forced out the outlet vents (24) and into the surrounding environment. The size and speed of the fan (36), the amount and properties of the substance, and the size and geometry of the body (12) and vents (22, 24) all affect the range and rate of dispersed substance.

Figure 4A:
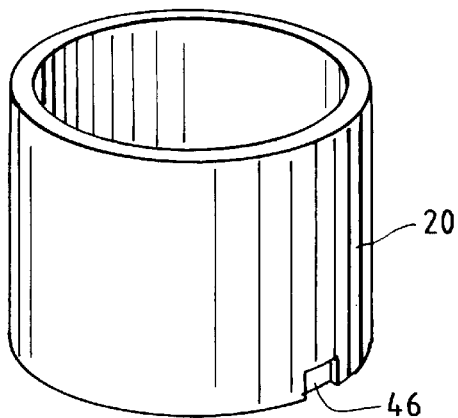
FIG. 4A is a perspective view of a component of the present invention.
Figure 4B:
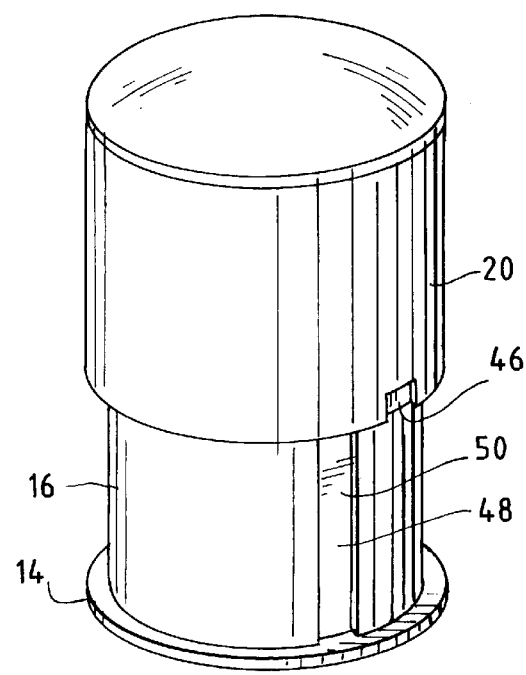
FIG. 4B is a perspective view of the substance dispersing apparatus of the present invention, shown in a closed position.

As shown in FIGS. 2A, 2B, 4A and 4B, the slideable section (20) can be fitted with an electrical switch arrangement comprising a recessed portion (46) having a conventional electrical conductor tip (not shown) on the inner surface of the slideable section (20) that is adapted to contact an electrical contact surface (48) on the base (14). When the slideable section (20) is moved to the "on" position, the conductor tip of the recessed portion (46) and surface (48) contact and create a closed circuit that causes electricity to flow from the batteries (42) to the DC motor (40) to operate the fan blade (36). A groove (50) extending vertically along the outside of the body (12) may be added to facilitate alignment of the contact surface (48) and the conductor tip. The groove (50) may further facilitate locking of the slideable section (20) in the opened position, as the apparatus may be constructed so that the recessed portion (46) and the groove (50) must be aligned in order to allow the slideable section (20) to translate relative to the body (12). For example, in the preferred embodiment, the slideable section (20) is adapted to be rotated when it is slid to the top (18) such that the recessed portion (46) and groove (50) are not aligned as shown in FIG. 4b, thereby prohibiting translation of the slideable surface (20) relative to the body (12). Such a switch arrangement facilitates easy use for a person wearing gloves, such as a hunter, and ensures that the fan (36) will not inadvertently operate when the apparatus (10) is in the off or closed position. In addition, the above described example of the present invention preferred embodiment provides a way of simultaneously shielding the substance carrying pad (30) from the environment while the apparatus (10) is in the closed, non-operating position, and exposing it when the apparatus in the opened, operating position. Alternatively, a conventional electrical switch (not shown) may be used.

Figure 5:
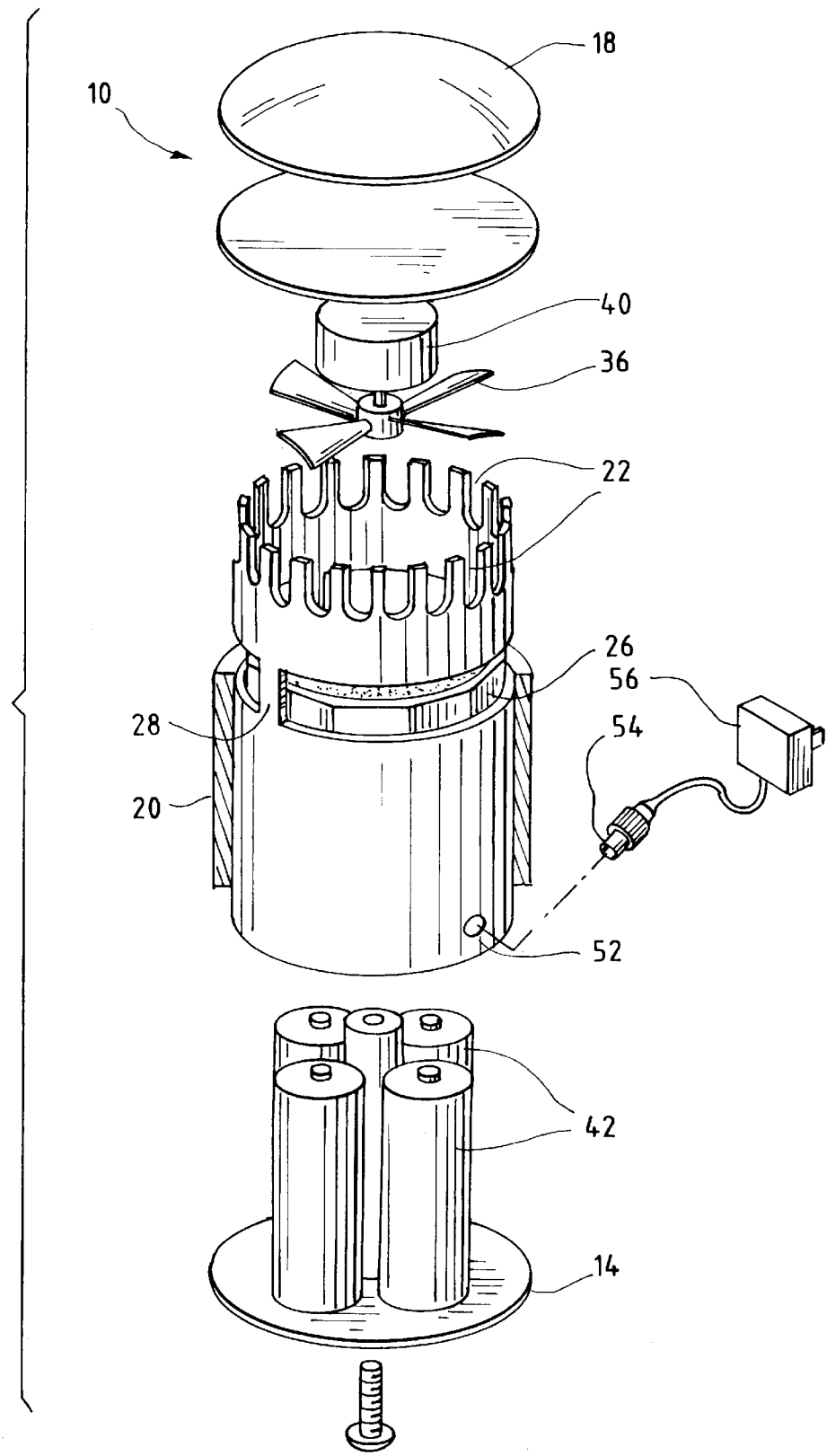
FIG. 5 is an exploded view of the present invention.

As shown in FIG. 5, the present invention apparatus (10) may be provided with an electric power jack (52), such as a conventional AC adapter (56) for plugging into and drawing power from an ordinary alternating current electrical outlet (not shown), or for supplying electricity to a conventional rechargeable unit (not shown) or conventional rechargeable batteries.

Figure 6C:
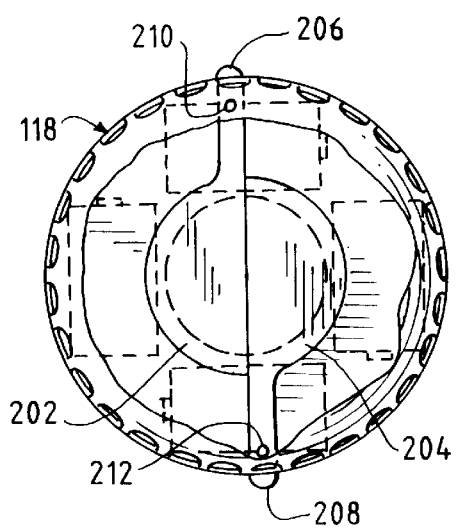
FIGS. 6C–6D are top views of the component of FIGS. 6A–6B.
Figure 6D:
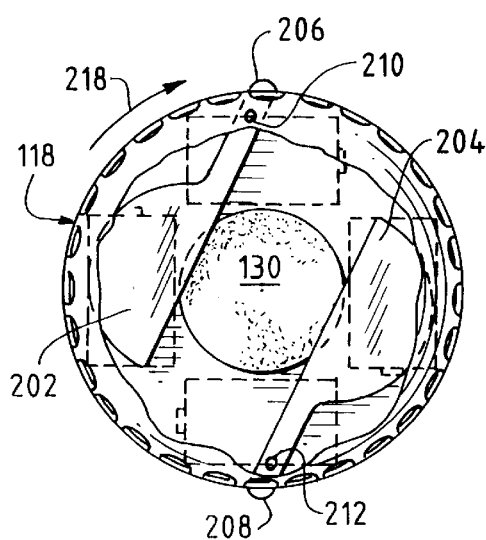
Figure 6A:
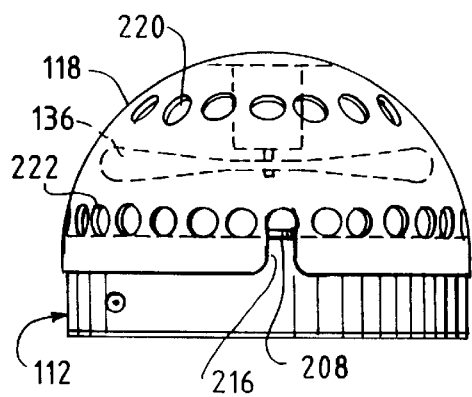
FIGS. 6A–6B are partial, front views of a component of a second embodiment of the present invention.
Figure 6B:
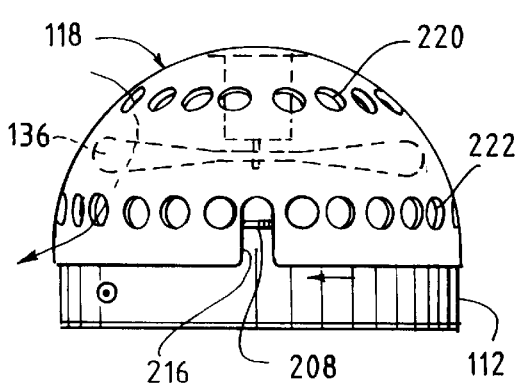

An alternative embodiment of the present invention apparatus is shown in FIGS. 6A, 6B, 6C and 6D. A modified top portion (118) is provide with a two-piece substance carrying structure (126) comprising first and second halves (202, 204). Each half (202, 204) is hollowed and adapted to receive approximately half of an absorbent pad (130), such that the halves (202, 204) can be joined shut in a substantially air-tight manner to encase the pad (130) as shown in FIGS. 6A–6C. Each half (202, 204) is provided with an extending portion (206, 208). A pivot connection in the form of a pin (210, 212) is provided for pivotally attaching each half (202, 204) to the body (112). The extending portions (206, 208) are adapted to extend through slots (214, 216) on the periphery of the dome (118) so that when the dome (118) is selectively rotated relative to the body (112) the extending portions (206, 208) are engaged and will move. As the dome (118) is moved in the direction of the arrow (218) shown in FIG. 6D, the halves (202, 204) are caused to pivot, thereby spreading apart into an opened position exposing the pad (130) to the outside environment.

Further shown in FIGS. 6A and 6B are a first set of holes (220) and a second set of holes (222) on the dome (118). Either set (220, 222) can serve as inlet vents, while the other serves as outlet vents, depending on the orientation of the rotating blade (136). When the first set of holes (220) is used as outlet or exhaust vents, the outside air is drawn in through the second set of holes (222), gathers vapors from the substance carrying pad (130), and is exhausted through the first set of holes (220) in a generally vertical direction, with an outwardly horizontal component tending to radially disperse. When the second set of holes (222) are used to exhaust, the intake air comes in through the holes (220) and is blown from the fan blade (136) against the pad (130) and then forced by pressure out through the second set of holes (222) primarily in a radial direction, in a generally level horizontal plane.

While the preferred embodiment has been herein described, it is understood that various modification and alternative design selection will not depart from the scope of the claimed invention.

What is claimed is:

1. A portable apparatus for dispersing a vapor from a volatile insect repellant or animal attracting/repelling substance into the surrounding environment, said apparatus comprising a cylindrical-shaped body having inlet and outlet vent means for the intake and exhaust of air into and out of said body;

sealing means for selectively closing and opening said inlet and said outlet vent means;

a disc-shaped substance containing means for containing said volatile insect repelling or animal attracting/repelling substance within said cylindrical-shaped body and being adapted to be inserted and removed from the cylindrical-shaped body when said inlet and said outlet vent means are open;

motorized fan means contained within said body for creating an air current and directing said air current into contact with said substance, and for creating air pressure causing said air current to carry vapors or particles from said substance out of said body through said outlet vent means, and an electrical power source contained within said body for providing electrical power to said motorized fan means.

* * * * *